United States Patent [19]

Aloup et al.

[11] 4,456,758

[45] Jun. 26, 1984

[54] HETEROCYCLIC NITRILES

[75] Inventors: Jean-Claude Aloup, Villeneuve-le-Roi; Jean Bouchaudon, Morsang-sur-Orge; Daniel Farge, Thiais; Claude James, Paris, all of France

[73] Assignee: Rhone-Poulenc Sante, Courbevoie, France

[21] Appl. No.: 406,998

[22] Filed: Aug. 10, 1982

[30] Foreign Application Priority Data

Aug. 11, 1981 [FR] France ................................ 81 15527

[51] Int. Cl.³ .................. C07D 409/04; C07D 407/04
[52] U.S. Cl. .................................... 546/284; 544/238; 544/283; 544/335; 544/336; 544/353; 546/122; 546/176; 546/268; 546/283; 548/336
[58] Field of Search ............... 544/238, 335, 283, 336, 544/353; 546/122, 176, 268, 283, 284; 548/336

[56] References Cited

U.S. PATENT DOCUMENTS 4,272,534  6/1981  Aloup et al. .................. 424/248.51
4,379,154  4/1983  Aloup et al. .......................... 424/250

Primary Examiner—Dolph H. Torrence
Attorney, Agent, or Firm—Stevens, Davis, Miller & Mosher

[57] ABSTRACT

New heterocyclic nitriles of the formula:

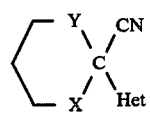

wherein (i) Het represents a heterocyclic radical of aromatic character containing one or two nitrogen atoms selected from pyrid-3-yl, pyrid-4-yl, pyridazinyl, pyrazinyl, pyrimidinyl, quinolyl, imidazolyl, naphthyridinyl, quinoxalinyl and quinazolinyl, X represents an oxygen atom and Y represents a valency bond or a methylene radical, or altenatively X represents a sulphur atom and Y represents a sulphur atom, a valency bond or a methylene radical, or (ii) Het represents the pyrid-2-yl radical, X represents an oxygen atom and Y represents a valency bond or a methylene radical, or alternatively X represents a sulphur atom and Y represents a sulphur atom or a methylene radical, are useful, in particular, as intermediates for the preparation of therapeutically useful heterocyclic thioformamides by converting the depicted cyano radical into a grouping —CSNHR wherein R represents a hydrogen atom or an alkyl ($C_{1-4}$) radical.

4 Claims, No Drawings

HETEROCYCLIC NITRILES

DESCRIPTION

The present invention relates to new heterocyclic nitriles of the general formula:

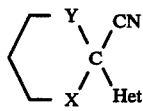

wherein (i) Het represents a heterocyclic radical of aromatic character containing one or two nitrogen atoms selected from pyrid-3-yl, pyrid-4-yl, pyridazinyl, pyrazinyl, pyrimidinyl, quinolyl, imidazolyl, naphthyridinyl, quinoxalinyl and quinazolinyl, X represents an oxygen atom and Y represents a valency bond or a methylene radical, or alternatively X represents a sulphur atom and Y represents a sulphur atom, a valency bond or a methylene radical, or (ii) Het represents the pyrid-2-yl radical, X represents an oxygen atom and Y represents a valency bond or a methylene radical, or alternatively X represents a sulphur atom and Y represents a sulphur atom or a methylene radical.

According to a feature of the present invention, the nitriles of general formula (I) wherein (a) Het represents a heterocyclic radical of aromatic character containing one or two nitrogen atoms selected from pyrid-3-yl, pyrid-4-yl, pyridazinyl, pyrazinyl, pyrimidinyl, quinolyl, imidazolyl, naphthyridinyl, quinoxalinyl and quinazolinyl, X represents a sulphur atom and Y represents a sulphur atom, a valency bond or a methylene radical, or (b) Het represents the pyrid-2-yl radical, X represents a sulphur atom and Y represents a sulphur atom or a methylene radical, are prepared by reacting a thiocyanate of the general formula:

wherein Z represents a halogen atom (e.g. chlorine, bromine or iodine) or another reactive ester radical (e.g. mesyloxy or tosyloxy) and n represents 3 or 4, or alternatively Z represents a thiocyanato radical and n represents 3, with a nitrile of the general formula:

wherein Het has the corresponding definition.

The reaction is generally carried out in an organic solvent, such as an aromatic hydrocarbon (e.g. benzene, toluene, xylene) or a chlorinated hydrocarbon (e.g. methylene chloride), in the presence of a phase transfer reagent, such as a tetraalkylammonium or trialkylbenzylammonium hydroxide or salt, in an aqueous solution of an alkali metal hydroxide at a temperature between 20° and 70° C. with vigorous stirring. In practice, it is preferred to use triethylbenzylammonium chloride in a 50% aqueous solution of sodium hydroxide.

The thiocyanates of general formula (II) can be prepared in accordance with the method of R. Adams and J. B. Campbell, J. Amer. Chem. Soc., 72, 128 (1950), or the method of L. Hagelbert, Chem. Ber., 23, 1083 (1890).

The nitriles of general formula (III) can be prepared in accordance with the method described by S. Okuda and M. M. Robison, J. Amer. Chem. Soc., 81, 740 (1959).

According to another feature of the present invention, the nitriles of general formula (I) wherein (a) Het represents a heterocyclic radical of aromatic character containing one or two nitrogen atoms selected from pyrid-3-yl, pyrid-4-yl, pyridazinyl, pyrazinyl, pyrimidinyl, quinolyl, imidazolyl, naphthyridinyl, quinoxalinyl and quinazolinyl, X represents a sulphur or oxygen atom and Y represents a valency bond or a methylene radical, or (b) Het represents the pyrid-2-yl radical, X represents a sulphur or oxygen atom and Y represents a methylene radical, or alternatively X represents an oxygen atom and Y represents a valency bond, are prepared by cyclising a heterocyclic derivative of the general formula:

wherein X and Het have the corresponding definitions and m represents 3 or 4.

The reaction is generally carried out in an organic solvent, such as an aromatic hydrocarbon (e.g. benzene, toluene, xylene) or a chlorinated hydrocarbon (e.g. methylene chloride), in the presence of carbon tetrachloride and of a phase transfer reagent, such as a tetraalkylammonium or trialkylbenzylammonium hydroxide or salt, in an aqueous solution of an alkali metal hydroxide at a temperature between 20° and 70° C. with vigorous stirring. In practice, it is preferred to use triethylbenzylammonium chloride in a 50% aqueous solution of sodium hydroxide.

The heterocyclic derivatives of general formula (IV) can be prepared by condensing a compound of the general formula:

wherein $Z_1$ represents a halogen atom (e.g. chlorine, bromine or iodine) or another reactive ester radical (e.g. mesyloxy or tosyloxy) and X and m have the corresponding definitions, with a nitrile of general formula (III).

It is to be understood that the thiol or alcohol function of the compounds of general formula (V) must be blocked beforehand by a labile protecting radical and then freed after condensation with the nitrile of general formula (III). The protecting radical can be any radical which is stable in an alkaline medium and which can easily be removed from the intermediate product without affecting the rest of the molecule. It is particularly advantageous to carry out the blocking with a tetrahydropyranyl radical [according to L. A. Paquette and M. K. Scott, J. Amer. Chem. Soc., 94, 6751 (1972)].

The condensation of the compound of the general formula (V), having the thiol or alcohol function blocked beforehand, with the nitrile of general formula (III) can be carried out by any method known per se for condensing a halogen derivative or a reactive ester (e.g. mesylate or tosylate) with a compound having an active methylene group. It is particularly advantageous to carry out the reaction in an organic solvent, such as an aromatic hydrocarbon (e.g. benzene, toluene, xylene) or a chlorinated hydrocarbon (e.g. methylene chloride) in the presence of a phase transfer reagent, such as a tetraalkylammonium or trialkylbenzylammonium hydroxide or salt, in an aqueous solution of an alkali metal hydroxide at a temperature between 20° C. and 70° C. with vigorous stirring. In practice, it is preferred to use triethylbenzylammonium chloride in a 50% aqueous solution of sodium hydroxide.

The new heterocyclic nitriles of general formula (I) are useful, in particular, as intermediates for the preparation of thioformamides of the general formula:

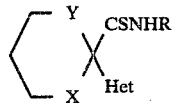 (IX)

wherein R represents a hydrogen atom or a straight- or branched-chain alkyl radical containing 1 to 4 carbon atoms and Het, X and Y are as hereinbefore defined.

To obtain the thioformamides of general formula (IX), the heterocyclic nitriles according to the invention can be used in the following way:

(i) The nitrile of general formula (I) is hydrolysed to the corresponding acid of the general formula:

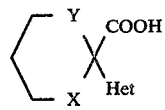 (X)

(wherein Het, X and Y are as hereinbefore defined) by any method known per se for converting a nitrile to an acid without affecting the rest of the molecule. (2) Ammonia or an amine of the general formula:

 R'—NH$_2$ (XI)

(wherein R' represents a straight- or branched-chain alkyl radical containing 1 to 4 carbon atoms) is condensed with the acid of the general formula (X) to give a formamide of the general formula:

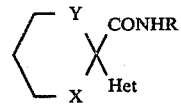 (XII)

wherein the various symbols are as hereinbefore defined.

In practice, ammonia or the amine of the general formula (XI) is generally reacted with the acid of general formula (X) in the presence of N,N'-carbonyl-diimidazole or dicyclohexylcarbodiimide, at a temperature of about 20° C. in an inert organic solvent, such as acetonitrile, methylene chloride, dimethylformamide or ethyl acetate, or with a halide of the acid of general formula (X) at a temperature between 0° and 50° C. in an organic solvent, such as an ether, tetrahydrofuran or a chlorinated hydrocarbon, in the presence of an acid acceptor, which can be an excess of ammonia or of the amine of general formula (XI), or alternatively pyridine or triethylamine.

(3) The formamide of general formula (XII) is converted to a corresponding thioformamide of general formula (IX) by means of a thionating reagent.

As the thionating reagent, it is particularly advantageous to use phosphorus pentasulphide or, preferably, Pedersen-Lawesson's reagent [i.e. 2,4-bis-(4-methoxyphenyl)-2,4-dithioxo-1,3-dithia-2,4-diphosphetane] prepared according to B. S. Pedersen, S. Scheibye, N. H. Nilsson and S. O. Lawesson, Bull. Soc. Chim. Belge, 87, 223 (1978). The reaction is generally carried out in an organic solvent which is inert towards the thionating reagent, such as an aromatic hydrocarbon (e.g. benzene, toluene, xylene), an ether (e.g. dioxan), a chlorinated hydrocarbon (e.g. chlorobenzene) or pyridine, at a temperature between 50° C. and the reflux temperature of the reaction mixture.

The new nitriles according to the present invention, and also the thioformamides of general formula (IX) prepared therefrom can be purified by the usual physical methods, in particular crystallisation and chromatography.

The thioformamides of general formula (IX) prepared from the products according to the invention possess particularly useful pharmacological properties coupled with a low toxicity. They exhibit an antisecretory anti-ulcer activity and/or an activity regulating the cardiovascular system (antihypertensive agents).

The thioformamides of general formula (IX) which more particularly possess anti-ulcer properties of the antisecretory type are those in which Het represents a heterocyclic radical of aromatic character, containing one or two nitrogen atoms, attached via a carbon atom located in the α-position to a nitrogen atom, and selected from pyridazin-3-yl, pyrazinyl, pyrimidin-2-yl or pyrimidin-4-yl, quinol-2-yl, imidazol-2-yl or imidazol-4-yl, 1,8-naphthyridin-2-yl, quinoxalin-2-yl, quinazolin-2-yl and quinazolin-4-yl, X represents an oxygen atom and Y represents a valency bond or a methylene radical, or alternatively X represents a sulphur atom and Y represents a sulphur atom, a valency bond or a methylene radical, or Het represents the pyrid-2-yl radical, X represents an oxygen atom and Y represents a valency bond or a methylene radical, or alternatively X represents a sulphur atom and Y represents a sulphur atom or a methylene radical.

These properties can be demonstrated in rats at doses of between 1 and 100 mg/kg animal body weight, administered orally, in particular using the technique of Rossi et al., C.R. Soc. Biol., 150, 2124 (1956), and that of Shay et al., Gastroenterology, 5, 43 (1945). Their lethal dose (LD$_{50}$) in mice is generally more than 300 mg/kg animal body weight, administered orally.

The thioformamide derivatives of general formula (IX) which are more especially valuable as anti-ulcer agents are those in which the symbol Het, as it has just been defined, represents the pyrid-2-yl, quinol-2-yl or pyridazin-3-yl radical.

The following compounds are very particularly valuable: N-methyl-2-(quinol-2-yl)-tetrahydrothiophene-2-carbothioamide, N-methyl-2-(pyrid-2-yl)-tetrahydrothiopyran-2-carbothioamide, N-methyl-2-(pyrid-2-yl)-1,3-dithiane-2-carbothioamide, N-methyl-2-(pyrid-2-yl)-tetrahydrofuran-2-carbothioamide, 2-(pyrid-2-yl)-1,3-dithiane-2-carbothioamide and N-methyl-2-(pyridazin-3-yl)-tetrahydrothiophene-2-carbothioamide.

The thioformamides of general formula (IX) which more particularly possess properties regulating the cardiovascular system (antihypertensive agents) are those wherein Het represents a heterocyclic radical of aromatic character, containing one or two nitrogen atoms, attached via a carbon atom located in the β-position to a nitrogen atom, and selected from pyrid-3-yl, pyridazin-4-yl, pyrimidin-5-yl, quinol-3-yl, imidazol-5-yl or 1,8-naphthyridin-3-yl, X represents an oxygen atom and Y represents a valency bond or a methylene radical, or alternatively X represents a sulphur atom and Y represents a sulphur atom, a valency bond or a methylene radical. At doses of between 0.1 and 100 mg/kg animal body weight, administered orally, they lower the blood pressure in spontaneously hypertensive rats (SHR rats) of the Okamoto-Aoki strain. The use of spontaneously hypertensive rats for studying antihypertensive products is described by J. L. Roba, Lab. Anim. Sci., 26, 305 (1976).

The thioformamides of general formula (IX) which are more especially valuable as antihypertensive agents are those in which the symbol Het represents the pyrid-3-yl or quinol-3-yl radical.

The following are very particularly valuable as antihypertensive agents: N-methyl-2-(pyrid-3-yl)-tetrahydrothiophene-2-carbothioamide, N-methyl-2-(pyrid-3-yl)-tetrahydrothiopyran-2-carbothioamide and N-methyl-2-(quinol-3-yl)-tetrahydrothiophene-2-carbothioamide.

The following non-limitative Examples illustrate how the present invention can be put into practice.

EXAMPLE 1

A solution of sodium hydroxide pellets (216 g) in distilled water (216 cc), and then triethylbenzylammonium chloride (6.5 g), are added, with stirring, to a solution of pyrid-3-yl-acetonitrile (156 g) in toluene (430 cc). A solution of 3-bromopropyl thiocyanate (282 g) in toluene (430 cc) is then added dropwise in the course of 20 minutes, the temperature being kept below 52° C. After stirring for 1 hour at 67° C. and cooling to 30° C., the reaction mixture is decanted and the aqueous phase is diluted with distilled water (200 cc) and extracted twice with ethyl acetate (600 cc in total). The organic phases are combined and washed twice with distilled water (600 cc in total) and then twice with a 5N aqueous solution of hydrochloric acid (500 cc in total). The hydrochloric acid extracts are combined, washed twice with ethyl acetate (600 cc in total) and neutralised by adding a 10N solution of ammonia (500 cc) in the presence of ethyl acetate (500 cc). After decantation, the aqueous phase is extracted twice with ethyl acetate (500 cc in total). The organic extracts are combined, washed 3 times with distilled water (600 cc in total), dried over anhydrous sodium sulphate and concentrated to dryness under reduced pressure (20 mm Hg; 2.7 kPa) at 60° C. The product obtained (215 g) is dissolved in boiling diisopropyl ether (1600 cc), and the solution, treated with decolorising charcoal (2 g), is filtered hot and the filtrate is then kept for 3 hours at 0° C. The resulting crystals are filtered off, washed with diisopropyl ether (150 cc) and dried under reduced pressure (20 mm Hg; 2.7 kPa) at a temperature of about 20° C. This gives 2-(pyrid-3-yl)-tetrahydrothiophene-2-carbonitrile (145 g) melting at 45° C.

3-Bromopropyl thiocyanate can be prepared in accordance with the method described in the literature by R. Adams and J. B. Campbell [J. Amer. Chem. Soc., 72, 128 (1950)].

Pyrid-3-yl-acetonitrile can be prepared in accordance with the method described in the literature by S. Okuda and M. M. Robison ]J. Amer. Chem. Soc., 81, 740 (1959)].

EXAMPLE 2

A solution of α-(3-hydroxypropyl)-pyrid-3-yl-acetonitrile (27.5 g) in toluene (30 cc) is added, in the course of 10 minutes and at a temperature not exceeding 40° C., to a stirred mixture of carbon tetrachloride (120 cc), sodium hydroxide pellets (100 g) dissolved beforehand in distilled water (100 cc), and triethylbenzylammonium chloride (2 g). After stirring for 1 hour at a temperature of about 20° C., distilled water (250 cc) is added and the reaction mixture is extracted 3 times with methylene chloride (600 cc in total). The organic extracts are combined, washed twice with distilled water (400 cc in total), dried over anhydrous sodium sulphate and concentrated to dryness under reduced pressure (20 mm Hg; 2.7 kPa) at 40° C. The product obtained (13 g) is chromatographed on neutral silica gel (75 g) contained in a column of diameter 3.4 cm. Elution is carried out with a cyclohexane/ethyl acetate mixture (70/30 by volume), one 200 cc fraction and one 3.5 liter fraction being collected. The latter is concentrated to dryness under reduced pressure (20 mm Hg; 2.7 kPa) at 40° C. This gives 2-(pyrid-3-yl)-tetrahydrofuran -2-carbonitrile (10 g) in the form of a yellow oil.

(Rf=0.6; chromatography on a thin layer of silica gel; solvent: ethyl acetate).

α-(3-Hydroxypropyl)-pyrid-3-yl-acetonitrile can be prepared in the following manner:

A solution of α-[3-(tetrahydropyran-2-yloxy)-propyl]-pyrid-3-yl-acetonitrile (43 g) in a 1N aqueous solution of hydrochloric acid (800 cc) is kept for about 16 hours at a temperature of the order of 20° C. The reaction mixture is then extracted 3 times with ethyl acetate (750 cc in total), and a 10N aqueous solution of sodium hydroxide is then added slowly so as to adjust the pH of the medium to between 8 and 9, the temperature being kept below 20° C. The mixture is extracted 3 times with ethyl acetate (900 cc in total) and the organic extracts are combined, washed with distilled water (250 cc), dried over anhydrous sodium sulphate and concentrated to dryness under reduced pressure (20 mm Hg; 2.7 kPa) at 40° C. This gives α-(3-hydroxypropyl)-pyrid-3-yl-acetonitrile (27.5 g) in the form of a yellow oil.

(Rf=0.35; chromatography on a thin layer of silica gel; solvent: ethyl acetate).

α-[3-(Tetrahydropyran-2-yloxy)propyl]-pyrid-3-yl-acetonitrile can be prepared in the following manner:

A solution of sodium hydroxide pellets (40 g) in distilled water (40 cc), and then triethylbenzylammonium chloride (2.5 g), are added to a solution of pyrid-3-yl-acetonitrile (23.9 g) in toluene (50 cc). The mixture is stirred and a solution of 1-bromo-3-(tetrahydropyran-2-yloxy)propane (51.3 g) in toluene (30 cc) is added dropwise in the course of 15 minutes, the temperature being kept below 50° C. After stirring for 1 hour 30 minutes at a temperature of about 40° C. and then for 15 hours at a temperature of about 20° C., distilled water (200 cc) is added and the mixture is extracted 3 times with methylene chloride (450 cc in total). The organic extracts are combined, washed 3 times with distilled water (450 cc in total), dried over anhydrous sodium sulphate and concentrated to dryness under reduced pressure (20 mm Hg; 2.7 kPa) at 40° C. The product obtained (56.7 g) is chromatographed on neutral silica gel (500 g) contained in a column of diameter 5 cm. Elution is carried out successively with a cyclohexane/ethyl acetate mixture (80/20 by volume; 3 liters) and with a cyclohexane/ethyl acetate mixture (30/70 by volume; 9 liters), one 3 liter fraction and one 9 liter fraction being collected. The latter is concentrated to dryness under reduced pressure (20 mm Hg; 2.7 kPa) at 50° C. This gives α-[3-(tetrahydropyran-3-yloxy)propyl]-pyrid-3-yl-acetonitrile (43 g) in the form of a yellow oil.

(Rf=0.55; chromatography on a thin layer of silica gel; solvent: ethyl acetate).

1-Bromo-3-(tetrahydropyran-2-yloxy)-propane can be prepared as described in the literature by L. A. Paquette and M. K. Scott [J. Amer. Chem. Soc., 94, 6751 (1972)].

EXAMPLE 3

A solution of sodium hydroxide pellets (65.3 g) in distilled water (65 cc), and then triethylbenzylammonium chloride (1.63 g), are added, with stirring, to a solution of pyrid-3-yl-acetonitrile (40 g) in toluene (120 cc), the temperature being kept below 30° C. A solution of 4-bromobutyl thiocyanate (73.5 g) in toluene (120 cc) is then added dropwise in the course of 25 minutes, the temperature being kept below 45° C. After stirring for 1 hour 30 minutes at 54° C. and cooling to 25° C., the reaction mixture is decanted. The organic phase is washed 5 times with distilled water (750 cc in total) and then with a 2N aqueous solution of hydrochloric acid (250 cc). The hydrochloric acid extracts are combined, washed 3 times with diethyl ether (450 cc in total), treated with decolorising charcoal (0.7 g) and filtered, and the filtrate is rendered alkaline by adding a 10N aqueous solution of sodium hydroxide (60 cc). The aqueous phase is extracted 4 times with diethyl ether (800 cc in total). The ether extracts are combined, washed 3 times with distilled water (450 cc in total), dried over anhydrous magnesium sulphate, treated with decolorising charcoal (1 g) and filtered, and the filtrate is concentrated to dryness under reduced pressure (20 mm Hg; 2.7 kPa) at 50° C.. The product obtained (35 g) is chromatographed on a column of diameter 3.6 cm, containing silica (0.063–0.2 mm; 180 g), elution being carried out first with pure methylene chloride (3 liters) and then with a methylene chloride/methanol mixture (99.5/0.5 by volume; 500 cc) and 500 cc fractions being collected. The first fraction is discarded. The next 6 fractions are combined and concentrated to dryness under reduced pressure (20 mm Hg; 2.7 kPa) at 40° C. This gives 2-(pyrid-3-yl)-tetrahydrothiopyran-2-carbonitrile (18.3 g) in the form of an orange oil, which crystallises from diisopropyl ether (m.p. 75° C.).

[Rf=0.47; chromatography on a thin layer of silica gel; solvent: cyclohexane/ethyl acetate (50/50 by volume)].

4-Bromobutyl thiocyanate can be prepared in accordance with the method described in the literature by R. Adams and D. C. Blomstrom [J. Amer. Chem. Soc., 75, 2375 (1953)].

Pyrid-3-yl-acetonitrile can be prepared in accordance with the method described in the literature by S. Okuda and M. M. Robison [J. Amer. Chem. Soc., 81, 740 (1959)].

The heterocyclic nitriles of general formula (I) can be used for the preparation of the thioformamides of general formula (IX) by following the procedure described in the ensuing USE Examples.

USE EXAMPLE 1

A solution of 2-(pyrid-3-yl)-tetrahydrothiophene-2-carbonitrile (34 g) in a 10N aqueous solution of hydrochloric acid (320 cc) is heated for 3 hours at 70° C. with stirring. After stirring for a further 15 hours at a temperature of about 20° C., the reaction mixture is concentrated to dryness under reduced pressure (1 mm Hg; 0.13 kPa) at 70° C. The product obtained (48 g) is dissolved in distilled water (150 cc), and the solution is treated with a 10N solution of ammonia (20 cc). The resulting precipitate is filtered off, washed with distilled water (25 cc) and then twice with diisopropyl ether (100 cc in total) and dried under reduced pressure (20 mm Hg; 2.7 kPa) at a temperature of about 20° C. This gives a product (31 g) which is dissolved in boiling ethanol (210 cc); the solution, treated with decolorising charcoal (0.5 g), is filtered hot and the filtrate is then kept for 1 hour at 0° C. The resulting crystals are filtered off, washed with ethanol (20 cc) and then twice with diisopropyl ether (40 cc in total) and dried under reduced pressure (20 mm Hg; 2.7 kPa) at a temperature of about 20° C. The product obtained (18 g) is redissolved in a 1N aqueous solution of sodium hydroxide (87 cc). The solution is washed 3 times with chloroform (150 cc in total), treated with decolorising charcoal (0.5 g) and filtered. A 10N aqueous solution of hydrochloric acid (about 6 cc) is then added to the filtrate so as to adjust the pH to 4. The resulting crystals are filtered off, washed with distilled water (10 cc) and dried under reduced pressure (1 mm Hg; 0.13 kPa) at a temperature of about 20° C. The product obtained (13.9 g) is dissolved in boiling ethanol (130 cc), the solution is filtered hot and the filtrate is then kept for 3 hours at a temperature of about 5° C. The resulting crystals are filtered off, washed twice with diisopropyl ether (40 cc in total) and dried under reduced pressure (1 mm Hg; 0.13 kPa) at 60° C. This finally gives 2-(pyrid-3-yl)-tetrahydrothiophene-2-carboxylic acid (11.5 g) melting at 184° C.

2-(Pyrid-3-yl)-tetrahydrothiophene-2-carboxylic acid (58.5 g), obtained as described above, is added in small portions, in the course of 15 minutes, to thionyl chloride (90 cc) to which dimethylformamide (0.1 cc) has been added. The reaction mixture is then stirred at the boil for 2 hours, cooled to a temperature of about 20° C. and then concentrated to dryness under reduced pressure (20 mm Hg; 2.7 kPa) at 70° C. This gives crude 2-chloroformyl-2-(pyrid-3-yl)-tetrahydrothiophene hydrochloride (75 g) in the form of a yellow solid, which is used immediately without further purification.

The 2-chloroformyl-2-(pyrid-3-yl)-tetrahydrothiophene hydrochloride thus obtained (3.5 g) is dissolved in methylene chloride (35 cc). The solution obtained is then saturated (2 hours) with a stream of anhydrous monomethyl amine, the temperature of the reaction mixture being kept at about 20° C. After stirring for 16 hours at the same temperature, a saturated aqueous solution of sodium bicarbonate (40 cc) is added, the mixture is decanted and the aqueous phase is extracted 3 times with methylene chloride (75 cc in total). The organic extracts are combined, washed 3 times with distilled water (60 cc in total), dried over anhydrous sodium sulphate and concentrated to dryness under reduced pressure (20 mm Hg; 2.7 kPa) at 50° C. The product obtained (1.9 g) is dissolved in boiling diisopropyl ether (175 cc), and the solution, treated with decolorising charcoal (0.3 g), is filtered hot and the filtrate, after cooling, is then kept for 3 hours at a temperature of about 5° C. The melting crystals are filtered off, washed with diisopropyl ether (2 cc) and dried under reduced pressure (20 mm Hg; 2.7 kPa) at 20° C. The product obtained (1.2 g), to which the product prepared in the same manner in another operation (1.2 g) has been added, is dissolved in boiling diisopropyl ether (250 cc), and the solution, treated with decolorising charcoal (0.2 g), is filtered hot and the filtrate, after cooling, is kept for 15 hours at a temperature of about 5° C. The resulting crystals are filtered off, washed twice with diisopropyl ether (6 cc in total) and dried under reduced pressure (1 mm Hg; 0.13 kPa) at 60° C. This gives N-methyl-2-(pyrid-3-yl)-tetrahydrothiophene-2-carboxamide (1.95 g) melting at 123° C.

2,4-bis-(4-Methoxyphenyl)-2,4-dithioxo-1,3-dithia-2,4-diphosphetane (9.3 g) is added to a solution of the N-methyl-2-(pyrid-3-yl)-tetrahydrothiophene-2-carboxamide prepared as described above (6.8 g) in toluene (90 cc). The suspension obtained is heated at the boil for 3 hours. The mixture is then cooled to a temperature of about 20° C. and treated with distilled water (100 cc), ethyl acetate (120 cc) and a 10N aqueous solution of ammonia (10 cc). After decantation, the aqueous phase is extracted twice with ethyl acetate (240 cc in total). The organic extracts are combined and washed 3 times with distilled water (150 cc in total), dried over anhydrous sodium sulphate and concentrated under reduced pressure (20 mm Hg; 2.7 kPa) at 60° C. The product obtained (7.5 g) is dissolved in boiling ethanol (40 cc), and the solution, treated with decolorising charcoal (0.1 g), is filtered hot and the filtrate, after cooling, is then kept for 1 hour at a temperature of about 5° C. The resulting crystals are filtered off, washed with ethanol (4 cc) and then twice with diisopropyl ether (20 cc in total) and dried under reduced pressure (1 mm Hg; 0.13 kPa) at 60° C. This gives N-methyl-2-(pyrid-3-yl)-tetrahydrothiophene-2-carbothioamide (4.9 g) melting at 133° C.

USE EXAMPLE 2

A solution of 2-(pyrid-3-yl)-tetrahydrofuran-2-carbonitrile (10 g) in a 10N aqueous solution of hydrochloric acid (100 cc) is heated for 3 hours at a temperature of between 60° C. and 70° C. and then concentrated to dryness under reduced pressure (20 mm Hg; 2.7 kPa) at 60° C.

The resulting mixture of the intermediate acid hydrochloride and ammonium chloride is dissolved in thionyl chloride (50 cc) containing dimethylformamide (0.1 cc). After heating at the boil for 1 hour 15 minutes, the reaction mixture is concentrated to dryness under reduced pressure (20 mm Hg; 2.7 kPa) at 40° C., and methylene chloride (200 cc) is then added. The insoluble crystals are removed by filtration and the filtrate is concentrated to dryness under reduced pressure (20 mm Hg; 2.7 kPa) at 40° C. This gives 2-chloroformyl-2-(pyrid-3-yl)-tetrahydrofuran (12.9 g) in the form of a light brown oil.

This hydrochloride is dissolved in methylene chloride (130 cc). A stream of anhydrous monomethylamine is bubbled into the resulting solution up to saturation (3 hours), the temperature being kept at about 20° C. Distilled water (100 cc) is then added and, after decantation, the organic phase is washed with distilled water (100 cc), dried over anhydrous sodium sulphate and concentrated to dryness under reduced pressure (20 mm Hg; 2.7 kPa) at 40° C. The product obtained (6.8 g) is chromatographed on neutral silica gel (70 g) contained in a column of diameter 3 cm. Elution is carried out with a cyclohexane/ethyl acetate mixture (70/30 by volume; 3 liters) and then with ethyl acetate (5 liters), one 3 liter fraction and one 5 liter fraction being collected. The latter is concentrated to dryness under reduced pressure (20 mm Hg; 2.7 kPa) at 50° C. This gives crude N-methyl-2-(pyrid-3-yl)-tetrahydrofuran-2-carboxamide (5.2 g) melting at 107° C.

2,4-bis-(4-Methoxyphenyl)-2,4-dithioxo-1,3-dithia-2,4-diphosphetane (7.7 g) is added to a solution of N-methyl-2-(pyrid-3-yl)-tetrahydrofuran-2-carboxamide prepared as described above (5 g) in toluene (120 cc), and the suspension obtained is heated at the boil for 2 hours. The reaction mixture is then cooled to a temperature of about 20° C. and then treated with distilled water (100 cc), a 10N aqueous solution of ammonia (100 cc) and ethyl acetate (100 cc). After decantation, the aqueous phase is extracted with ethyl acetate (50 cc) and the organic extracts are combined, washed with distilled water (100 cc), dried over anhydrous sodium sulphate and concentrated to dryness under reduced pressure (20 mm Hg; 2.7 kPa) at 50° C. The product obtained (6.7 g) is chromatographed on neutral silica gel (75 g) contained in a column of diameter 3 cm. Elution is carried out successively with a cyclohexane/ethyl acetate mixture (80/20 by volume; 1500 cc) and with a cyclohexane/ethyl acetate mixture (60/40 by volume; 2400 cc), thirteen 300 cc fractions being collected. Fractions 6 to 13 are combined and concentrated to dryness under reduced pressure (20 mm Hg; 2.7 kPa) at 50° C. The product obtained (3.5 g) is dissolved in methylene chloride (50 cc), and the solution is extracted 5 times with a 2N aqueous solution of hydrochloric acid (125 cc in total). The acid extracts are combined, washed twice with methylene chloride (40 cc in total) and brought to a pH of about 8 by adding a 10N aqueous solution of sodium hydroxide (25 cc). The mixture is then extracted 4 times with methylene chloride (200 cc in total), and the organic extracts are combined, washed twice with distilled water (100 cc in total), dried over anhydrous sodium sulphate and concentrated to dryness under reduced pressure (20 mm Hg; 2.7 kPa) at 40° C. The product obtained (2 g) is dissolved in a boiling diisopropyl ether/ethanol mixture (80/20 by volume; 40 cc), and the solution, treated with decolorising charcoal (0.1 g), is filtered hot and the filtrate, after cooling, is then kept for 1 hour at 0° C. The resulting crystals are filtered off, washed twice with diisopropyl ether (10 cc in total) and dried under reduced pressure (1 mm Hg; 0.13 kPa) at 60° C. This gives N-methyl-2-(pyrid-3-yl)-tetrahydrofuran-2-carbothioamide (1.5 g) melting at 128° C.

USE EXAMPLE 3

A solution of 2-(pyrid-3-yl)-tetrahydrothiopyran-2-carbonitrile (18 g) in a 12 N aqueous solution of hydrochloric acid (180 cc) is heated for 20 hours at 80° C. with stirring. After cooling to a temperature of about 20° C., the reaction mixture is concentrated to dryness under reduced pressure (20 mm Hg; 2.7 kPa) at 70° C. The crude product obtained is dissolved in distilled water (50 cc), and the solution prepared in this way is treated with decolorising charcoal (0.1 g) and filtered, and the filtrate is treated with a 7.5N solution of ammonia (about 17.5 cc) until the pH reaches 3.7, and kept for 1 hour at a temperature of about 5° C. The resulting precipitate is filtered off, washed 3 times with iced distilled water (30 cc in total) and dried under reduced pressure (20 mm Hg; 2.7 kPa) at a temperature of about 20° C. in the presence of potassium hydroxide pellets and then in air. This gives 2-(pyrid-3-yl)-tetrahydrothiopyran-2-carboxylic acid (16.6 g) melting at 193°–194° C.

The 2-(pyrid-3-yl)-tetrahydrothiopyran-2-carboxylic acid thus obtained (16.4 g) is added in small portions, in the course of 30 minutes, to thionyl chloride (25 cc) to which dimethylformamide (0.05 cc) has been added.

The reaction mixture is then stirred at the boil for 2 hours 30 minutes, cooled to a temperature of about 20° C. and then concentrated to dryness under reduced pressure (20 mm Hg; 2.7 kPa) at 70° C. This gives crude 2-chloroformyl-2-(pyrid-3-yl)-tetrahydrothiopyran hydrochloride (26 g) in the form of an orange oil, which is used immediately without further purification.

This product is dissolved in methylene chloride (70 cc). The solution obtained is then saturated (2 hours) with a stream of anhydrous monomethylamine, the temperature of the reaction mixture being kept at about 20° C. After stirring for 16 hours at the same temperature, the precipitate obtained is filtered off and washed 3 times with methylene chloride (90 cc in total). The organic filtrates are combined, washed 5 times with distilled water (250 cc in total), dried over anhydrous magnesium sulphate, treated with decolorising charcoal (0.2 g) and filtered, and the filtrate is concentrated to dryness under reduced pressure (20 mm Hg; 2.7 kPa) at 60° C. This gives an oily residue (16.3 g), which is chromatographed on a column of diameter 3.4 cm, containing silica (0.063–0.2 mm; 165 g), elution being carried out with ethyl acetate and 100 cc fractions being collected. The first 4 fractions are discarded. The next 10 fractions are combined and concentrated to dryness under reduced pressure (20 mm Hg; 2.7 kPa) at 60° C. This gives a crude product (14 g), which is dissolved in boiling acetonitrile (20 cc). This solution, after cooling, is kept for 1 hour at a temperature of about 5° C. The resulting crystals are filtered off, washed 3 times with diisopropyl ether cooled to about 5° C. (20 cc in total), and dried under reduced pressure (20 mm Hg; 2.7 kPa) at a temperature of about 20° C. in the presence of potassium hydroxide pellets. This gives N-methyl-2-(pyrid-3-yl)-tetrahydrothiopyran-2-carboxamide (11.3 g) melting at 109° C.

2,4-bis-(4-Methoxyphenyl)-2,4-dithioxo-1,3-dithia-2,4-diphosphetane (7.5 g) is added to a suspension of N-methyl-2-(pyrid-3-yl)-tetrahydrothiopyran-2-carboxamide prepared as described above (5.9 g) in toluene (75 cc). The suspension obtained is heated at the boil for 6 hours with stirring. After stirring for a further 16 hours at a temperature of about 20° C., the reaction mixture is treated with distilled water (80 cc), ethyl acetate (80 cc) and a 15N solution of ammonia (8 cc). After decantation, the aqueous phase is extracted 3 times with ethyl acetate (300 cc in total). The organic extracts are combined and washed 4 times with distilled water (320 cc in total), dried over anhydrous magnesium sulphate, treated with decolorising charcoal (0.5 g) and filtered, and the filtrate is concentrated to dryness under reduced pressure (20 mm Hg; 2.7 kPa) at 70° C. The product obtained (6.4 g) is dissolved in boiling ethanol (15 cc). The solution, after cooling, is kept for 30 minutes at a temperature of about 5° C. The resulting crystals are filtered off, washed twice with ethanol cooled to a temperature of about 5° C. (14 cc in total) and then twice with diisopropyl ether (20 cc in total) and dried under reduced pressure (20 mm Hg; 2.7 kPa) at a temperature of about 20° C. in the presence of potassium hydroxide pellets. This gives a crude product (4.6 g) melting at 120° C.

This product is dissolved in a 0.5N aqueous solution of hydrochloric acid (40 cc). The solution thus obtained is extracted 3 times with ethyl acetate (75 cc in total), treated with decolorising charcoal (0.1 g) and filtered, and the filtrate is rendered alkaline with a 2N aqueous solution of sodium hydroxide (12 cc) in the presence of ethyl acetate (25 cc). After decantation, the aqueous phase is extracted twice with ethyl acetate (50 cc in total). The organic extracts are combined, washed 3 times with distilled water (60 cc in total), dried over anhydrous magnesium sulphate and filtered, and the filtrate is concentrated to dryness under reduced pressure (20 mm Hg; 2.7 kPa) at 60° C. The product obtained (3.3 g) is dissolved in boiling ethanol (9 cc). The solution, after cooling, is kept for 30 minutes at a temperature of about 5° C. The resulting crystals are filtered off, washed twice with ethanol cooled to a temperature of about 50° C. (6 cc in total), and dried under reduced pressure (1 mm Hg; 0.13 kPa) at 60° C. This gives N-methyl-2-(pyrid-3-yl)-tetrahydrothiopyran-2-carbothioamide (2.6 g) melting at 124° C.

By following the procedure of Use Example 1 but starting from the corresponding nitriles of general formula (I) the following thioformamide products of general formula (IX) are obtained.

USE EXAMPLE 4

N-Methyl-2-(pyrid-4-yl)-tetrahydrothiophene-2-carbothioamine melting at 178° C.

USE EXAMPLE 5

N-Methyl-2-(quinol-2-yl)-tetrahydrothiophene-2-carbothioamine melting at 124° C.

USE EXAMPLE 6

N-Methyl-2-(pyrid-2-yl)-tetrahydrothiopyran-2-carbothioamide melting at 153° C.

USE EXAMPLE 7

2-(Pyrid-2-yl)-1,3-dithian-2-carbothioamide melting at 214° C.

USE EXAMPLE 8

N-Methyl-2-(pyrid-2-yl)-1,3-dithian-2-carbothioamide melting at 159° C.

USE EXAMPLE 9

N-Methyl-2-(pyrazin-2-yl)-tetrahydrothiophene-2-carbothioamide melting at 127° C.

USE EXAMPLE 10

N-Methyl-2-(pyrid-2-yl)-tetrahydrofuran-2-carbothioamide melting at 115° C.

USE EXAMPLE 11

N-Methyl-2-(pyridazin-3-yl)-tetrahydrothiophene-2-carbothioamide melting at 199° C.

USE EXAMPLE 12

N-Methyl-2-(quinol-3-yl)-tetrahydrothiophene-2-carbothioamide melting at 159° C.

We claim:

1. A heterocyclic nitrile of the formula:

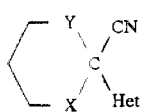

wherein
(i) Het represents a heterocyclic radical of aromatic character containing one or two nitrogen atoms selected from pyrid-3-yl, pyrid-4-yl, pyridazinyl, pyrazinyl, pyrimidinyl, quinolyl, imidazolyl, naphthyridinyl, quinoxalinyl and quinazolinyl, X represents oxygen and Y represents a valency bond or a methylene radical, or alternatively X represents sulphur and Y represents sulphur, a valency bond or a methylene radical, or (ii) Het represents the pyrid-2-yl radical, X represents oxygen and Y represents a valency bond or a methylene radical, or alternatively X represents sulphur and Y represents sulphur or a methylene radical.

2. A heterocyclic nitrile according to claim 1 which is 2-(pyrid-3-yl)-tetrahydrothiophene-2-carbonitrile.

3. A heterocyclic nitrile according to claim 1 which is 2-(pyrid-3-yl)-tetrahydrofuran-2-carbonitrile.

4. A heterocyclic nitrile according to claim 1 which is 2-(pyrid-3-yl)-tetrahydrothiopyran-2-carbonitrile.

* * * * *